United States Patent [19]

Janssen et al.

[11] Patent Number: 5,072,042

[45] Date of Patent: Dec. 10, 1991

[54] PHENYLHYDRAZONES, THE MANUFACTURE THEREOF AND THERAPEUTIC AND COSMETIC COMPOSITIONS PREPARED THEREFROM

[75] Inventors: Bernd Janssen, Ludwigshafen; Hans-Heiner Wuest, Dossenheim, both of Fed. Rep. of Germany; William V. Murray, Belle Mead; Michael P. Wachter, Bloomsbury, both of N.J.; Stanley Bell, Narberth, Pa.

[73] Assignee: BASF Aktiengesellschaft, Ludwigshafen, Fed. Rep. of Germany

[21] Appl. No.: 476,770

[22] Filed: Feb. 8, 1990

[30] Foreign Application Priority Data

Feb. 10, 1989 [DE] Fed. Rep. of Germany ....... 3903990

[51] Int. Cl.$^5$ ............................................. C07C 243/18
[52] U.S. Cl. ..................... 564/251; 558/176; 558/418; 560/34; 560/251; 562/439; 564/148; 544/159; 544/54; 544/298; 546/242
[58] Field of Search ............ 564/249, 251, 148; 558/176, 418; 560/34, 251; 562/439; 544/159, 54, 298; 546/242

[56] References Cited

U.S. PATENT DOCUMENTS

| | | |
|---|---|---|
| 2,350,718 | 6/1944 | Bretschneider et al. ............ 564/249 |
| 3,809,675 | 5/1974 | Hansen ................................ 564/251 |
| 3,829,492 | 8/1974 | Miller et al. ......................... 564/249 |
| 3,939,147 | 2/1976 | Hugelin et al. ...................... 564/249 |
| 4,265,784 | 5/1981 | Mailer et al. ........................ 564/249 |
| 4,326,055 | 4/1982 | Loeliger .............................. 564/251 |
| 4,588,750 | 5/1986 | Boris ................................... 504/251 |
| 4,732,904 | 3/1988 | Morgan ............................... 564/251 |

FOREIGN PATENT DOCUMENTS

| | | | |
|---|---|---|---|
| 498090 | 10/1970 | Switzerland ........................ | 564/251 |
| 2164938 | 4/1986 | United Kingdom ................ | 564/251 |

OTHER PUBLICATIONS

The Retinoids, vol. 2, pp. 391-409, G. L. Peck, "Synthetic Retinoids in Dermatology", 1984.
The Medical Journal of Australia, vol. 146, Jan. to Jun. 1987, pp. 374-377, R. Marks, et al., "The Oral Retinoid Agents".
Drugs, 34, pp. 459-503 (1987), C. E. Orfanos, et al., "The Retinoids, A Review of Their Clinical Pharmacology and Therapeutic Use".
Chemical Abstracts, vol. 71, pp. 331-332 (1969), 112535a.
Chemical Abstracts, vol. 89, p. 531 (1978) 89:179065n.
Chemical Abstracts, vol. 105, pp. 673-674 (1986), 105:42099f.

Primary Examiner—James H. Reamer
Attorney, Agent, or Firm—Oblon, Spivak, McClelland, Maier & Neustadt

[57] ABSTRACT

Phenylhydrazones of formula I

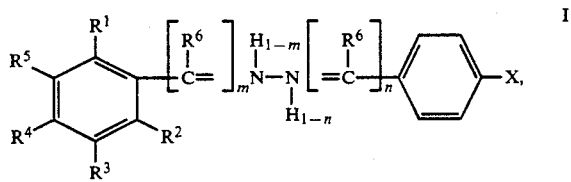

in which $R^1$ to $R^6$ and m and n have the meanings stated above, and the manufacture thereof. The substances are suitable for combating disease and for cosmetic use.

8 Claims, No Drawings

PHENYLHYDRAZONES, THE MANUFACTURE THEREOF AND THERAPEUTIC AND COSMETIC COMPOSITIONS PREPARED THEREFROM

U.S. Pat. No. 4,326,055, G.B. Pat. No. 2,164,938 and U.S. Pat. No. 4,588,750 reveal that stilbene derivatives in which the polyene structure of vitamin A-type substances is fixed in aromatic rings have a pharmacological action when used for topical or systemic treatment of neoplasia, acne, psoriasis and other dermatological disorders. However, the activity of these compounds is not always satisfactory [cf. G. L. Peck in The Retinoids, Vol. II, 391–409, Ed.: M. B. Sporn et al., Academic Press N.Y. (1984) or R. Marks et al., Med. J. Australia 146, 374–377 (1987) or C. E. Orfanos et al., Drugs 34, 459–503 (1987)].

It is an object of the invention to provide compounds having an improved range of activity. We have found that, surprisingly, this object is achieved with novel phenylhydrazones of formula I

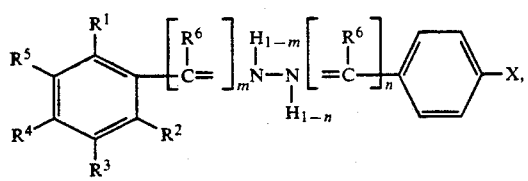

in which
R$^1$, R$^2$, and R$^3$ are independently of each other hydrogen, halogen, C$_1$–C$_4$-alkyl, hydroxyl, C$_1$–C$_4$-alkoxy or acetoxy,
R$_4$ is hydrogen, hydroxyl, C$_1$–C$_6$-alkyl, C$_1$–C$_6$-alkoxy or C$_2$–C$_6$-alkoxyalkyl, R$^5$ is hydrogen or C$_1$–C$_4$-alkyl, or R$^4$ and R$^5$ together form a ring which is —C(CH$_3$)$_2$—A—C(CH$_3$)$_2$— (where A is —CH$_2$CH$_2$—, —CH(CH$_3$)—, —CH$_2$C(O)— or —CH$_2$CHOH—) or is —(CH$_2$)$_3$C(CH$_3$)$_2$—, —OCH$_2$CH$_2$C(CH$_3$)$_2$—, —C(CH$_3$)$_2$CH(CH$_3$)CH$_2$C(CH$_3$)$_2$— or —NH-C(O)CH$_2$C(CH$_3$)$_2$—, provided that R$^4$ and R$^5$ together form a ring of the type specified or R$^4$ is branched C$_4$–C$_6$-alkoxy or branched C$_4$–C$_6$-alkoxyalkyl when R$^1$, R$^2$ and R$^3$ are each hydrogen,
R$^6$ is hydrogen, methyl, ethyl or cyclopropyl, m and n are different and denote 0 or 1,
X is hydrogen, nitro, methoxy or nitrile, a sulfonic acid radical or —CONR$^7$OR$^7$, —CO$_2$R$^7$, —PO-(OR$^8$)$_2$, —S(O)$_n$R$^8$ (where n is 0 or 2), —SO$_2$—NR$^9$R$^{10}$ or —CONR$^9$R$^{10}$, where R$^7$ is hydrogen, C$_1$–C$_3$-alkyl or phenyl, which may or may not be substituted by one or two amino, C$_1$–C$_4$-acylamino, C$_1$–C$_4$-alkyl or C$_1$–C$_4$-alkoxy groups, R$_8$ is C$_1$–C$_3$-alkyl and R$^9$ and R$^{10}$ are independently of each other hydrogen or C$_1$–C$_4$-alkyl or together form a piperidine, piperazine, morpholine or thiomorpholine ring, provided that R$^4$ and R$^5$ together form a ring of the type specified or H$^3$ and R$^5$ are each isopropyl, isobutyl or tert.butyl when X is hydrogen or nitro, and their physiologically tolerated salts.

Preferred compounds of formula I are those in which R$^1$ and
R$^2$ stand for hydrogen and R$^3$ and R$^5$ are each alkyl, preferably branched, or R$^4$ and R$^5$ together form a ring.

Where R$^1$, R$^2$ or R$^3$ is halogen, fluorine and chlorine are preferred.

Other preferred compounds of formula I are those in which R$^6$ is hydrogen or methyl and those in which X is —CO$_2$R$^7$, —CONR$^7$OR$^7$, —S(O)$_n$R$^8$, —SO$_2$NR$^9$R$^{10}$ or —CONR$^9$R$^{10}$, special preference being given to those compounds in which R$^7$ is hydrogen and R$^8$ is methyl or ethyl.

Some of the novel compounds of formula I contain chiral centers and they are generally obtained in the form of diastereomer mixtures or racemates. These diastereomers may be separated, for example, by methods utilizing their differences in solubility or by column chromatographic methods, by which means they can be isolated in a pure form. Individual enantiomers may be obtained from the pairs of enantiomers by conventional means. Both these and the mixtures thereof (racemates) are within the scope of the present invention. Both the individual (homogeneous) diastereomers or enantiomers and the mixtures thereof can be used as therapeutic and cosmetic agents.

Some of the compounds of the invention have an acid hydrogen atom and can thus be converted with bases by usual methods to physiologically tolerated salts which are readily soluble in water. Examples of suitable salts are ammonium salts, alkalimetal, in particular sodium, potassium and lithium, salts, alkaline-earth metal, in particular calcium and magnesium, salts, and salts with suitable organic bases, e.g. with lower alkylamines, such as methylamine, ethylamine and cyclohexylamine, or with substituted lower alkylamines, in particular hydroxysubstituted alkylamines, such as diethanolamine, triethanolamine and tris(hydroxymethyl)aminomethane, and with piperidine or morpholine.

The present invention also relates to a process for the manufacture of the above compounds of formula I, wherein
a) carbonyl compounds of formula IIa:

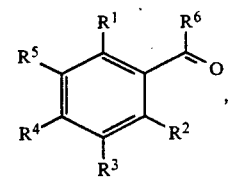

in which R$^1$ to R$^6$ have the meanings stated above, are condensed with phenylhydrazines of formula IIIa:

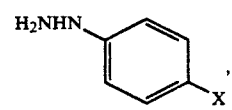

in which X has the meaning stated above, or
b) carbonyl compounds of formula IIb:

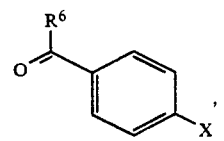

in which $R^6$ and X have the meanings stated above, are condensed with phenylhydrazines of formula IIIb:

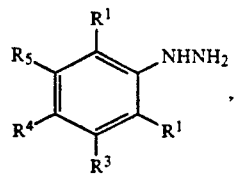

in which $R^1$ to $R^6$ have the meanings stated above.

The reaction is carried out in conventional manner (cf. for example "Methoden der Organischen Chemie" Ed.: Eugen Müller, Vol.VII,1, pp.461–466, Thieme Verlag, Stuttgart, 1954, Vol.VII,2b, pp.1954–1957, Thieme Verlag, Stuttgart, 1976 and Vol.X,2, pp.410–414, Thieme Verlag, Stuttgart, 967) in the presence or absence of a solvent or diluent, with or without the use of a catalyst and with or without the use of a water-binding agent, as required, and at temperatures ranging from 10° C. to the boiling point of the mixture, it being preferred to react the reactants II and III in equimolar amounts or, if desired, with an excess of one over the other of up to 15% molar.

Preferred solvents and diluents include hydrocarbons such as heptane, cyclohexane, toluene and xylene, lower aliphatic alcohols such as methanol, ethanol and isopropanol, further cyclohexanol, and ethylene glycol and its monoalkyl and dialkyl ethers, glycerol, ethers such as diethyl ether, diisopropyl ether and methyl-t-butyl ether, and tetrahydrofuran and dioxane. Further examples are acetic acid, amides such as dimethyl formamide and N-methylpyrrolidone, and pyridine, sulfolane and water or appropriate mixtures thereof.

Suitable catalysts are mineral acids such as hydrochloric and sulfuric acids, but preferably carboxylic acids such as acetic and trifluoroacetic acids and their alkali metal salts. However, bases such as pyridine and morpholine may also be used as catalysts.

Water-binding agents that may be used are inorganic salts such as anhydrous sodium carbonate and magnesium sulfate or, alternatively, molecular sieves. When working in lipophilic media it may be necessary to tap off the water of reaction.

The reaction is carried out at atmospheric or superatmospheric pressure.

The starting compounds of formula II are either known (cf., for example, DE-OS 3,602,473, DE-OS 3,434,942 and DE-OS 3,434,944) or are obtainable by conventional methods of preparing arylalkyl ketones, for example by Friedel-Crafts acylation (cf. H.0.House, "Modern Synthetic Reactions", 2nd Ed., W. A. Benjamin Inc. Menlo Park, CA,1972, pp.797 et sec. and the literature cited) or by oxidation of the appropriate alkylbenzenes (cf. H. O. House loc.cit., pp.288 et sec. and the literature cited), or by conventional methods of preparing benzaldehydes, for example by the formylation of aromatics as proposed by Vilsmeier (cf. De.Meheas, Bull.Soc.Chem.Fr pp.1989-1999 (1962) and the literature cited) or by reduction of the appropriate benzoyl halides (cf. Fuson in: Patai, "The Chemistry of the Carbonyl Group", Vol.1, pp.211-232, Interscience Publ. N.Y. 1966, or Wheeler in: patai, "The Chemistry of Acyl Halides", pp. 231-251, Interscience Publ. N.Y. 1972) or benzonitriles (cf. J. March, "Advanced Organic Chemistry", 2nd Ed. McGraw-Hill Kogakusha Ltd., Tokio, 1977, pp.835-836 and the literature cited).

The starting compounds of formula III are either known (cf."Methoden der Organischen Chemie", Ed. Eugen Müller, Vol.X2, pp.169-315, Thieme Verlag, Stuttgart 1967) or are obtainable by generally known methods of preparing aryl hydrazines.

The compounds of the invention and their physiologically tolerated salts have pharmacological properties which make them suitable for topical and systemic therapeutic and prophylactic treatment of precancerous stages and carcinomas of the skin, mucous membranes and internal organs and for the topical and systemic treatment of acne, psoriasis and other dermatological diseases associated with pathological changes in hornification, in particular ichthyosis, Darier's disease, herpes, leucoplakia, further vitiligo, eczema and warts, and also pale eyes and other disorders of the cornea, and for the treatment of rheumatic diseases, particularly those of an inflammatory or degenerative nature which involve joints, muscles, tendons and other areas of the locomotor system. A preferred range of indications includes, in addition to the treatment of dermatological diseases and skin lesions caused by the action of sunlight or by iatrogenic influence, for example atrophy induced by corticosteroids, the prophylactic treatment of precancerous stages and tumors.

The pharmacological effects may be demonstrated, for example, in the following test models: the compounds of the invention cancel keratinization following vitamine A deficiency as tested on trachial tissue of the hamster in vitro. Keratinization pertains to the early phase of carcinogenesis, which is inhibited by the compounds of formula I of the invention by a similar technique carried out in vivo following initiation of the pathological condition by chemical compounds or by energetic radiation or following viral cell transformation. This method of procedure is described in Cancer Res. 36, 964–972 (1972) and in Nature 250, 64–66 (1974) and Nature 253, 47–50 (1975).

In addition, the rate of proliferation of certain malignantly changed cells is inhibited by the compounds of the invention. This method of procedure is described in J. Natl. Cancer Inst. 60, 1035-1041 (1978), Experimental Cell Research 117, 15-22 (1978) and Proc. Sci. USA 77, 2937-2940 (1980).

The anti-arthritic effect of the compounds of the invention may be determined on animals by usual methods involving adjuvant arthritis or arthritis induced by cell walls of streptococci. The dermatological activity, e.g. for treatment of acne, may be demonstrated, for example, by the comedolytic activity of the compounds or by their ability to reduce the number of cysts induced in the rhinomouse.

This method is described by L. H. Kligman et al. in The Journal of Investigative Dermatology 73, 354-358 (1978).

Another measure of the dermatological activity is provided by the reduction of sebaceous glands and the resulting drop in sebaceous secretion in the hamster flank organ. This method of procedure is described by E. C. Gomez in J. Am. Dermatol. 6, 746–750 (1982).

Further, animal experiments can demonstrate the ability of the compounds of the invention to effect reversion of skin lesions caused by ultraviolet light. This method of procedure is described by L. H. Kligman et al. in Connect. Tissue Res. 12, 139-150 (1984) and in the Journal of the American Academy of Dermatology 15, 779-785 (1986).

Accordingly, the invention further relates to cosmetic and therapeutic agents for topical and systemic application, which contain, as active ingredient, a compound of formula I together with the usual vehicles or diluents, to the use of compounds of formula I for the preparation of therapeutic compositions and to their use in the manufacture of cosmetic preparations.

The agents are suitable for oral, parenteral and topical administration. Examples of suitable preparations are tablets, film tablets, dragées, capsules, pills, powders, solutions, suspensions, solutions for infusion or injection, and pastes, ointments, gels, creams, lotions, powders, solutions, emulsions and sprays.

The therapeutic agents for topical application and the cosmetic agents may contain the compounds to be used in accordance with the present invention in a concentration of from 0.001 to 0.1% and preferably from 0.001 to 0.1%, and the therapeutic agents for systemic administration may contain said compounds in a preferred amount of from 0.1 to 250mg per individual dose, one or more doses to be administered daily depending on the nature and severity of the disease.

The pharmaceutic and cosmetic preparations of the invention are prepared in conventional manner using conventional solid or liquid vehicles or diluents and conventional industrial adjuvants appropriate to the desired method of application, in suitable dosage forms. Forms suitable for oral administration are, for example, tablets, film tablets, dragées, capsules, pills, powders, solutions or suspensions or depot forms. Tablets may be obtained, for example, by blending the active ingredient with conventional adjuvants, e.g. inert diluents such as dextrose, sugar, sorbitol, mannitol and polyvinyl pyrrolidone, disintegrating agents such as corn starch and alginic acid, binding agents such as starch and gelatine, lubricants such as magnesium stearate and talcum and/or repository agents such as carboxypolymethylene, carboxymethyl cellulose, acetylcellulose phthalate and polyvinyl acetate. The tablets may consist of a number of layers.

Similarly, dragées can be made by coating a core produced in a manner similar to that described above for tablets, the coating agents being those normally used for dragée coatings, for example polyvinyl pyrrolidone or shellac, gum arabic, talcum, titanium dioxide and sugar. The dragée coating may also consist of a number of layers and the adjuvants mentioned above with respect to tablets may also be used.

Solutions or suspensions containing the active ingredients of the invention may also contain taste improvers, such as saccharine, cyclamate and sugar, and aromatics, e.g. vanillin and orange extract. They may also contain dispersing agents such as sodium carboxylmethyl cellulose or preservatives such as p-hydroxybenzoates. Capsules containing active ingredient may be prepared, for example, by mixing the active ingredient with an inert vehicle such as lactose or sorbitol and enclosing the mixture in gelatine capsules.

Examples of suitable common ingredients of cosmetic and therapeutic preparations for topical application are as follows:

anionic, cationic and non-ionic emulsifiers and emulsion stabilizers, which may at the same time act as consistency improvers or gel formers, such as polyvinyl pyrrolidone, fatty alcohols, glycerol monostearate, polyacrylic acids, cellulose derivatives and ethylene oxide/propylene oxide block polymers;

solid or liquid oily or fatty substances of mineral, vegetable or animal origin and synthetic oily esters such as triglyceride ester and isopropyl myristate;

hydrophilic components such as glycerol, polyethylene glycol and propylene glycol.

Further examples of ingredients for cosmetics are sunscreens, suntanning agents, preservatives, antioxidants, pigments, dyes, ethereal oils, perfume oils, vitamins, vegetable extracts, collagen, etc.. These substances can be found, for example, in CTFA, Cosmetic Ingredient Dictionary, 3rd Edition, Washington 1982.

Preparation of the starting materials

EXAMPLE A 1,4-Dimethoxy-2-formyl-5,6,7,8-tetrahydro-5,5,8,8-tetramethylnaphthalene 92.9g (0.37 mole) of 1,4-dimethoxy-5,6,7,8,tetrahydro5,5,8,8-tretramethylnaphthalene and 52.5g (0.37 mole) of hexamethylene tetramine were refluxed for 2 hours in 350ml of trifluoroacetic acid. The reaction solution was concentrated in vacuo, the residue poured onto ice, neutralized with solid sodium carbonate and extracted with ether. The extracts were washed with water and dried over magnesium sulfate to give on evaporation of the solvent an oily residue. Purification by flash chromatography gave 45g of the above compound, which was recrystallized from heptane. M.p. 55°-57° C.

EXAMPLE B 1,1,2,3,3-Pentamethyl-2,3-dihydro-5(1H)-indenylcyclopropyl ketone

To a suspension, prepared with cooling, of 125g (0.94 mole) of anhydrous aluminum chloride in 185ml of dry methylene chloride there were added dropwise 125g (1.2 moles) of cyclopropyl carboxychloride followed, at 0° -5° C., by 158g (0.84 mole) of 1,1,2,3,3-pentamethyl-2,3-drihydro-(1H)-indane dissolved in 230ml of dry methylene chloride. The reaction solution was stirred overnight at 5° C., poured onto ice and extracted with methylene chloride. The extracts were washed with sodium carbonate solution and water till neutral, dried over sodium sulfate and concentrated. The oily residue gave after distillation 159g of the above compound as a colorless oil, B.p.$_{0.4}$; 120°-125° C., n$^{22}$ 1,5425.

EXAMPLE C 3,5-Di-t-butylphenylhydrazine 5.7g (50 mmoles) of hydroxylamine-O-sulfonic acid were added dropwise to 22g (0.107 mole) of 3,5-di-t-butylaniline in 20ml of water at 80° C. After cooling, the precipitate was separated by filtration under subatmospheric pressure and extracted with toluene by boiling. The residue was treated with 2N sodium hydroxide solution and extracted with methylene chloride, followed by evaporation of the solvent, to give an oil which was chromatographed on silica gel in a 10:1 n-heptane/ethyl acetate system. After separation of unconverted starting aniline, the target compound was eluted in a 10:3 n-heptane/acetic acid system. There were obtained 3.5g of an oil which formed, from ether, a colorless salt with ethereal hydrochloric acid, m.p. 196°-199° C.

Preparation of the end products

EXAMPLE 1

1,4-Dimethoxy-5,6,7,8-tetrahydro-5,5,8,8-tetramethyl-naphthyl-2-aldehyde-N-(4-carboxyphenyl) hydrazone 8.3g (30 mmoles) of 1,4-dimethoxy-2-formyl-5,6,7,8-tetrahydro-5,5,8,8-tetramethylnaphthalene (Example A) and 4.6g (30 mmoles) of phenylhydrazine-4-carboxylic acid were stirred under reflux in 75ml of tetrahydrofuran. On completion of the reaction the solvent was evaporated off. Recrystallization of the residue from methanol gave 8.5g of the above compound, m.p. 238°–245°C.

EXAMPLE 2

1,1,2,3,3-Pentamethyl-2,3-dihydro-5(1H)-indenyl-cyclopropylketone-N-(4-carboxyphenyl) hydrazone 7.7g (30 mmoles) of 1,1,2,3,3-pentamethyl-2,3-dihydro-5-(1H)-indenyl-cyclopropyl ketone (Example B) and 4.6g (30 mmoles) of phenylhydrazine-4-carboxylic acid were stirred under reflux in a mixture of 75ml of tetrahydrofuran, 10ml of ethanol and 2ml of glacial acetic acid. On completion of the reaction the solution was concentrated and the residue recrystallized from ethanol. There were obtained 3.9g of the above compound, m.p. 227°–231° C.

EXAMPLE 3

1,2,3,4-Tetrahydro-1,1,4,4-tetramethylnaphthalenyl-6-aldehyde-N-(4-carboxylphenyl) hydrazone 5.0g (23 mmoles) of 1,2,3,4-tetrahydro-1,1,4,4-tetra methylnaphthalenyl-6-aldehyde and 3.8q (25 mmoles) of phenylhydrazine-4-carboxylic acid were stirred for 1 hour under reflux in 50ml of tetrahydrofuran. After cooling, the reaction solution was poured onto heptane and the precipitate was filtered off and recrystallized from methanol. There were obtained 5.4g of the above compound, m.p. 260° C.

EXAMPLE 4

1,2,3,4-Tetrahydro-1,1,4,4-tetramethylnaphthenyl-6-methylketone-N-(4-carboxylphenyl) hydrazone 5.0g (22 mmoles) of 1,2,3,4-tetrahydro-1,1,4,4-tetramethylnaphthalenyl-6-methyl ketone and 3.8g (25 mmoles) of phenylhydrazine-4-carboxylic acid were reacted as in Example 3 to give, after recrystallization from ethanol, 3.5g of the above compound, m.p. 250° C.

EXAMPLE 5

4-Methoxycarbonylbenzaldehyde-N-(3,5-di-t-butylphenyl)hydrazone 3.5g (15 mmoles) of 3,5-di-t-butylphenylhydrazine and 2.6g (15 mmoles) of methyl 4-formylbenzoate were stirred for 1 hour under reflux in 150ml of a 1:1 mixture of tetrahydrofuran and ethanol. After evaporation of the solvent the residue was digested with ethanol at the boil and then cooled, filtered off in vacuo and rinsed with ethanol. After drying in vacuo at ambient temperature, there were obtained 3.2g of the above compound, m.p. 215°–220° C.

EXAMPLE 6

4-Carboxybenzaldehyde-N-(3,5-di-t-butylphenyl)hydrazone 2.2g of the ester obtained in Example 5 were refluxed with 3g of potassium hydroxide for 1 hour in 70ml of a 3:3:1 mixture of ethanol, dimethyl sulfoxide and water. The reaction mixture was poured into 140ml of ice water and adjusted to pH 2 with hydrochloric acid, whereupon the precipitate was filtered off in vacuo. After recrystallization from methanol, there were obtained 1.2g of the above compound, m.p. 208°–213° C.

The Examples listed in the following Table were carried out by methods similar to those described in Examples 1–6:

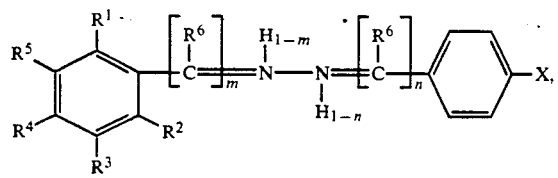 I

| No. | $R^1$ | $R^2$ | $R^3$ | $R^4$ | $R^5$ | m | n | $R^6$ | X | M.p. (°C.) |
|---|---|---|---|---|---|---|---|---|---|---|
| 7 | H | H | H | —C(CH$_3$)$_2$CH$_2$CH$_2$—C(CH$_3$)$_2$— | | 1 | 0 | H | OCH$_3$ | 142–146 |
| 8 | H | H | H | —C(CH$_3$)$_2$CH$_2$CH$_2$—C(CH$_3$)$_2$— | | 1 | 0 | H | NO$_2$ | 227–231 |
| 9 | H | H | H | —C(CH$_3$)$_2$CH$_2$CH$_2$—C(CH$_3$)$_2$— | | 1 | 0 | H | SO$_2$CH$_3$ | 228–233 |
| 10 | H | H | H | —C(CH$_3$)$_2$—CH$_2$CO—C(CH$_3$)$_2$— | | 1 | 0 | CH$_3$ | CO$_2$H | 275–279 |
| 11 | H | OH | C$_2$H$_5$ | H | C$_2$H$_5$ | 1 | 0 | CH$_3$ | CO$_2$H | 239–241 |
| 12 | H | CH$_3$ | H | —C(CH$_3$)$_2$—CH$_2$CH$_2$—C(CH$_3$)$_2$— | | 1 | 0 | H | CO$_2$H | 216–220 |
| 13 | H | H | H | —C(CH$_3$)$_2$—CH(CH$_3$)—C(CH$_3$)$_2$— | | 1 | 0 | C$_2$H$_5$ | CO$_2$H | 266–269 |
| 14 | H | H | H | —C(CH$_3$)$_2$—COCH$_2$—C(CH$_3$)$_2$— | | 1 | 0 | CH$_3$ | CO$_2$H | 302–305 |
| 15 | H | H | H | —C(CH$_3$)$_2$—CH(CH$_3$)—C(CH$_3$)$_2$— | | 1 | 0 | CH$_3$ | CO$_2$H | 268–274 |
| 16 | H | H | H | —NHCO—CH$_2$—C(CH$_3$)$_2$— | | 1 | 0 | CH$_3$ | CO$_2$H | |
| 17 | H | OCH$_3$ | H | —C(CH$_3$)$_2$—CH$_2$CH$_2$—C(CH$_3$)$_2$— | | 1 | 0 | CH$_3$ | CO$_2$H | 230–234 |
| 18 | H | CH$_3$ | H | —C(CH$_3$)$_2$—CH$_2$CH$_2$—C(CH$_3$)$_2$— | | 1 | 0 | CH$_3$ | CO$_2$H | 275–278 |
| 19 | H | H | H | —C(CH$_3$)$_2$—CH$_2$CH$_2$—C(CH$_3$)$_2$— | | 1 | 0 | CH$_2$\CH\CH$_2$ (cyclopropyl) | CO$_2$H | 243–245 |
| 20 | H | F | H | —C(CH$_3$)$_2$—CH$_2$CH$_2$—C(CH$_3$)$_2$— | | 1 | 0 | CH$_3$ | CO$_2$H | 256–260 |
| 21 | H | H | CH$_3$ | —OCH$_2$CH$_2$—C(CH$_3$)$_2$— | | 1 | 0 | CH$_3$ | CO$_2$H | |
| 22 | OC$_6$H$_{13}$ | CH$_3$ | H | —C(CH$_3$)$_2$—CH$_2$CH$_2$—C(CH$_3$)$_2$— | | 1 | 0 | H | CO$_2$H | 155–156 |
| 23 | H | H | H | —CH$_2$CH$_2$CH$_2$C(CH$_3$)$_2$— | | 1 | 0 | CH$_3$ | CO$_2$H | |
| 24 | OCH$_3$ | CH$_3$ | H | —C(CH$_3$)$_2$—CH$_2$CH$_2$—C(CH$_3$)$_2$— | | 1 | 0 | H | CO$_2$H | 220–223 |

-continued

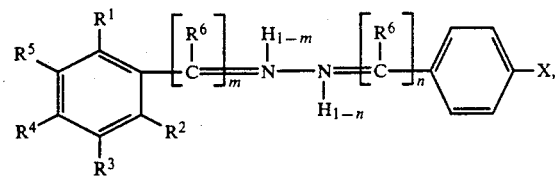

I

| No. | R¹ | R² | R³ | R⁴ | R⁵ | m | n | R⁶ | X | M.p. (°C.) |
|---|---|---|---|---|---|---|---|---|---|---|
| 25 | H | OCH₃ | H | —C(CH₃)₂—CH₂CH₂—C(CH₃)₂— | | 1 | 0 | H | CO₂H | 257–260 |
| 26 | OCH₃ | OCH₃ | H | —C(CH₃)₂—CH₂CH₂—C(CH₃)₂— | | 1 | 0 | H | SO₂CH₃ | 92–94 |
| 27 | H | F | H | —C(CH₃)₂—CH₂CH₂—C(CH₃)₂— | | 1 | 0 | H | CO₂H | 234–237 |
| 28 | H | H | C(CH₃)₃ | H | C(CH₃)₃ | 1 | 0 | H | CO₂H | 259–262 |
| 29 | OH | CH₃ | H | —C(CH₃)₂—CH₂CH₂—C(CH₃)₂— | | 1 | 0 | H | CO₂H | 297–300 |
| 30 | H | H | C(CH₃)₃ | OH | C(CH₃)₃ | 1 | 0 | H | CO₂H | 248–249 |
| 31 | H | H | H | —C(CH₃)₂—CH₂CH(OH)—C(CH₃)₂— | | 1 | 0 | H | CO₂H | 236–240 |
| 32 | H | H | H | C(CH₃)₃ | H | 1 | 0 | C₂H₅ | CO₂H | 212–215 |
| 33 | H | H | H | C(CH₃)₃ | H | 1 | 0 | CH₃ | CO₂H | 260–262 |
| 34 | H | H | OC(CH₃)₃ | H | H | 1 | 0 | CH₃ | CO₂H | 214–217 |
| 35 | H | H | CH(CH₃)₂ | OH | CH(CH₃)₂ | 1 | 0 | CH₃ | CO₂H | 217–220 |
| 36 | H | H | H | C(CH₃)₂OCH₃ | H | 1 | 0 | H | CO₂H | 196–200 |
| 37 | H | H | H | —C(CH₃)₂—CH₂CH₂—C(CH₃)₂— | | 1 | 0 | H | H | 80–82 |
| 38 | H | H | H | —C(CH₃)₂—CH₂CH₂—C(CH₃)₂— | | 1 | 0 | H | CN | |
| 39 | H | H | H | —C(CH₃)₂—CH₂CH₂—C(CH₃)₂— | | 1 | 0 | H | CO₂C₂H₅ | 207 |
| 40 | H | H | H | —C(CH₃)₂—CH₂CH₂—C(CH₃)₂— | | 1 | 0 | H | CON(CH₃)₂ | 223 |
| 41 | OAc | H | OAc | —C(CH₃)₂—CH₂CH₂—C(CH₃)₂— | | 1 | 0 | H | CO₂H | |
| 42 | OH | H | OH | —C(CH₃)₂—CH₂CH₂—C(CH₃)₂— | | 1 | 0 | H | CO₂H | |
| 43 | H | OAc | C₂H₅ | H | C₂H₅ | 1 | 0 | CH₃ | CO₂H | |
| 44 | H | H | H | —C(CH₃)₂—CH₂CH₂—C(CH₃)₂— | | 1 | 0 | H | SO₃H | 280 (decomposes) |
| 45 | H | CH₃ | H | —C(CH₃)₂—CH(CH₃)—CH₂—C(CH₃)₂— | | 1 | 0 | CH₃ | CO₂H | |
| 46 | H | H | H | —C(CH₃)₂—CH₂CH₂—C(CH₃)₂— | | 1 | 0 | CH₃ | SO₂CH₃ | 211–214 |
| 47 | H | H | H | —C(CH₃)₂—CH₂CH₂—C(CH₃)₂— | | 1 | 0 | H | SO₂C₂H₅ | 177–181 |
| 48 | H | H | H | —C(CH₃)₂—CH₂CH₂—C(CH₃)₃— | | 0 | 1 | H | SO₂C₂H₅ | 188–190 |
| 49 | H | H | H | —C(CH₃)₂—CH₂CH₂—C(CH₃)₃— | | 0 | 1 | H | CO₂CH₃ | 141–143 |
| 50 | H | H | H | —C(CH₃)₂—CH₂CH₂—C(CH₃)₃— | | 0 | 1 | H | CO₂H | 187–189 |
| 51 | OCH₃ | H | OCH₃ | —C(CH₃)₂—CH₂CH₂—C(CH₃)₂— | | 1 | 0 | H | SO₂CH₃ | 255–258 |
| 52 | H | OCH₃ | H | —C(CH₃)₂—CH₂CH₂—C(CH₃)₂— | | 1 | 0 | H | SO₂CH₃ | 232–236 |
| 53 | H | F | H | —C(CH₃)₂—CH₂CH₂—C(CH₃)₂— | | 1 | 0 | H | SO₂CH₃ | 244–247 |
| 54 | H | H | C(CH₃)₃ | H | C(CH₃)₃ | 1 | 0 | H | SO₂CH₃ | 190–192 |
| 55 | OCH₃ | CH₃ | H | —C(CH₃)₂—CH₂CH₂—C(CH₃)₂— | | 1 | 0 | H | SO₂CH₃ | 224–227 |
| 56 | OH | CH₃ | H | —C(CH₃)₂—CH₂CH₂—C(CH₃)₂— | | 1 | 0 | H | SO₂CH₃ | 331–335 |
| 57 | H | H | C(CH₃)₃ | OH | C(CH₃)₃ | 1 | 0 | H | SO₂CH₃ | 206–209 |
| 58 | H | F | H | —C(CH₃)₂—CH₂CH₂—C(CH₃)₂— | | 1 | 0 | CH₃ | SO₂CH₃ | 190–193 |
| 59 | H | H | H | —C(CH₃)₂—CH₂CH₂—C(CH₃)₂— | | 1 | 0 | H | CONHOH | |
| 60 | H | H | H | —C(CH₃)₂—CH₂CH₂—C(CH₃)₂— | | 1 | 0 | H | CONHOCH₃ | |
| 61 | H | H | H | —C(CH₃)₂—CH₂CH₂—C(CH₃)₂— | | 1 | 0 | CH₃ | CON(CH₃)OH | |
| 62 | H | H | C(CH₃)₃ | OH | C(CH₃)₃ | 1 | 0 | CH₃ | SO₂CH₃ | 233–236 |
| 63 | H | H | C(CH₃)₃ | OH | C(CH₃)₃ | 1 | 0 | CH₃ | CO₂H | 249–250 (decomposes) |
| 64 | H | H | H | —C(CH₃)₂—CH₂CH₂—C(CH₃)₂— | | 1 | 0 | H | PO(OCH₃)₂ | |
| 65 | H | H | C(CH₃)₃ | OH | C(CH₃)₃ | 1 | 0 | CH₃ | CO₂CH₃ | 180–182 |
| 66 | H | H | C(CH₃)₃ | OH | C(CH₃)₃ | 1 | 0 | CH₃ | SO₂C₂H₅ | 163 |
| 67 | H | H | C(CH₃)₃ | OH | C(CH₃)₃ | 1 | 0 | CH₃ | SO₂CH(CH₃)₂ | 120 |
| 68 | H | H | C(CH₃)₃ | OH | C(CH₃)₃ | 1 | 0 | CH₃ | CONH₂ | 212 |
| 69 | H | H | C(CH₃)₃ | OH | C(CH₃)₃ | 1 | 0 | CH₃ | CO₂C₂H₅ | 129–132 |
| 70 | H | H | C(CH₃)₃ | OH | C(CH₃)₃ | 1 | 0 | CH₃ | CO₂C₆H₅ | 209–210 |
| 71 | OCH₃ | OCH₃ | H | —C(CH₃)₂—CH₂CH₂—C(CH₃)₂ | | 1 | 0 | H | CO₂H | 171–174 |
| 72 | H | H | H | —C(CH₃)₂—CH₂CH₂—C(CH₃)₂ | | 1 | 0 | CH₃ | SO₂CH(CH₃)₂ | 156–159 |
| 73 | H | H | H | —C(CH₃)₃—CH₂CH₂—C(CH₃)₃ | | 1 | 0 | H | SO₂CH(CH₃)₂ | 205–206 |
| 74 | H | H | C(CH₃)₃ | H | C(CH₃)₃ | 1 | 0 | H | SO₂C₂H₅ | 222–224 |
| 75 | H | H | C(CH₃)₃ | H | C(CH₃)₃ | 1 | 0 | H | SO₂CH(CH₃)₂ | 203–205 |
| 76 | H | H | C(CH₃)₃ | OH | C(CH₃)₃ | 1 | 0 | CH₃ | SO₂N(piperidine) | |
| 77 | H | H | C(CH₃)₃ | OH | C(CH₃)₃ | 1 | 0 | CH₃ | SO₂N(piperazine-NH) | |

-continued $$\text{R}^5 \underset{\text{R}^3}{\overset{\text{R}^1}{\underset{\text{R}^4}{\bigcirc}}} \text{R}^2 \left[ \underset{\text{H}_{1-m}}{\overset{\text{R}^6}{\text{C}}} \right]_m = \text{N} - \text{N} = \left[ \underset{\text{H}_{1-n}}{\overset{\text{R}^6}{\text{C}}} \right]_n \bigcirc - \text{X},$$   I

| No. | R¹ | R² | R³ | R⁴ | R⁵ | m | n | R⁶ | X | M.p. (°C.) |
|-----|-----|-----|-----|-----|-----|---|---|-----|-----|-----|
| 78 | H | H | C(CH₃)₃ | OH | C(CH₃)₃ | 1 | 0 | CH₃ | SO₂N⟨O⟩ | |
| 79 | H | H | C(CH₃)₃ | OH | C(CH₃)₃ | 1 | 0 | CH₃ | CON⟨S⟩ | |
| 80 | OC₃H₇ | CH₃ | H | —C(CH₃)₂—CH₂CH₂—C(CH₃)₂ | | 1 | 0 | H | CO₂H | 199–200 |
| 81 | OC₂H₅ | CH₃ | H | —C(CH₃)₂—CH₂CH₂—C(CH₃)₂ | | 1 | 0 | H | CO₂H | 214–216 |
| 82 | H | H | H | —C(CH₃)₂—CH₂CH₂—C(CH₃)₂ | | 1 | 0 | H | SOCH₃ | |
| 83 | H | H | C(CH₃)₃ | OH | C(CH₃)₃ | 1 | 0 | H | SO₃H | |
| 84 | H | H | C(CH₃)₃ | H | C(CH₃)₃ | 1 | 0 | CH₃ | SO₃H | |

| | Rhino Mouse Assay | |
|---|---|---|
| Example | Dose (%) | Ultriculus Reduction |
| 4 | 0.01 | 70.8 |
| 3 | 0.01 | 70.3 |
| 15 | 0.01 | 74.0 |
| 8 | 0.1 | 34.2 |
| 9 | 0.2 | 65.4 |
| 10 | 0.001 | 56.7 |
| 11 | 0.1 | 70.6 |
| 13 | 0.01 | 65.0 |
| 19 | 0.01 | 63.4 |
| 33 | 0.1 | 66.1 |
| 34 | 0.01 | 43.7 |
| 35 | 0.01 | 37.3 |
| 26 | 0.1 | 14.5 |
| 49 | 0.01 | 53.2 |
| 1 | 0.01 | 59.1 |
| 2 | 0.01 | 54.2 |
| 12 | 0.01 | 66.1 |
| 31 | 0.01 | 65.0 |
| 72 | 0.1 | 74.6 |
| 20 | 0.01 | 74.2 |
| 46 | 0.1 | 75.1 |
| 18 | 0.01 | 46.9 |
| 37 | 0.1 | 19.6 |
| 32 | 0.01 | 28.9 |
| 6 | 0.01 | 63.1 |
| 51 | 0.1 | 35.5 |
| 52 | 0.1 | 33.8 |
| 53 | 0.1 | 33.8 |
| 53 | 0.1 | 67.9 |
| 55 | 0.1 | 34.5 |
| 56 | 0.1 | 37.6 |
| 50 | 0.01 | 50.3 |
| 48 | 0.1 | 34.3 |
| 58 | 0.1 | 47.7 |
| 62 | 0.1 | 46.2 |
| 46a | 0.1 | 71.6 |

Examples of pharmaceutical preparations

EXAMPLE I

Tablets containing 250mg of active ingredient
Recipe for 1,000 tablets:

| active ingredient from Example 2 | 250 g |
|---|---|
| potato starch | 100 g |
| lactose | 50 g |
| 4% gelatine solution | 45 g |
| talcum | 10 g |

Preparation

The finely powdered active ingredient, potato starch and lactose are mixed, and the mixture is thoroughly moistened with about 45g of 4% gelatine solution, finely granulated and dried. The dry granules are sifted, mixed with 10g of talcum and pressed into tablets in a rotary pelleting machine. The tablets are put into polypropylene containers which close tightly.

EXAMPLE II

Cream containing 0.1% of active ingredient:

| active ingredient from Example 7 | 0.1 g |
|---|---|
| glycerol monostearate | 10.0 g |
| cetyl alcohol | 4.0 g |
| polyethylene glycol 400-stearate | 10.0 g |
| polyethylene glycol sorbitan-monostearate | 10.0 g |
| propylene glycol | 6.0 g |
| methyl p-hydroxybenzoate | 0.2 g |
| demineralized water | to 100.0 g |

Preparation

The active ingredient is ground to a very fine powder and suspended in propylene glycol. The resulting suspension is stirred into a melt of glycerol monostearate, cetyl alcohol, polyethylene glycol 400-stearate and polyethylene glycol sorbitan-monostearate heated at 65° C. A solution of methyl p-hydroxybenzoate in water having a temperature of 70° C. is added to this mixture to form an emulsion. After cooling, the cream is homogenized in a colloid mill and filled into tubes.

EXAMPLE III

Powder containing 0.1% of active ingredient:

| | |
|---|---|
| active ingredient from Example 4 | 0.1 g |
| zinc oxide | 10.0 g |
| magnesium oxide | 10.0 g |
| highly dispersed silicon dioxide | 2.5 g |
| magnesium stearate | 1.0 g |
| talcum | 76.4 g |

Preparation

The active ingredient is micronized in an air jet mill and mixed homogeneously with the other ingredients. The mixture is pressed through a sieve (mesh width No.7) and filled into polyethylene containers having a sprinkler insert.

We claim:

1. Phenylhydramones of formula I:

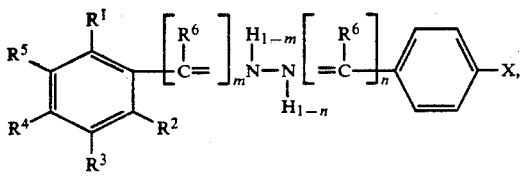

wherein $R^1$, $R^2$ and $R^3$ are independently of each other hydrogen, halogen,
$C_1$-$C_4$-alkyl, hydroxyl, $C_1$-$C_4$-alkoxy or acetoxy, $R^4$ is hydrogen, hydroxyl, tert-butyl, $C_1$-$C_6$-alkoyx or $C_2$-$C_6$-alakoxyalkyl;
$R^5$ is hydrogen or $C_1$-$C_4$-alkyl, or
$R^4$ and $R^5$ together form a ring which is —C(CH$_3$)$_2$—A—C(CH$_3$)$_2$—(where A is —CH$_2$CH$_2$—, —CH(CH$_3$)—, —CH$_2$C(O)— or —CH$_2$CHOH—) or is —(CH$_2$)$_3$C(CH$_3$)$_2$—, —OCH$_2$CH$_2$C(CH$_3$)$_2$—, —C(CH$_3$)$_2$CH(CH$_3$) CH$_2$C(CH$_3$)$_2$— or —NHC(O)CH$_2$C(CH$_3$)$_2$—, provided that $R^4$ and $R^5$ together form a ring of the type specified or $R^4$ is branched $C_4$-$C_6$-alkoxy or branched $C_4$-$C_6$-alkoxyalkyl when $R^1$, $R^2$ and $R^3$ are each hydrogen,
$R^6$ is hydrogen, methyl, ethyl or cyclopropyl, m and n are different and denote 0 or 1,
X is hydrogen, nitro, methoxy or nitrile, a sulfonic acid radical or —CONR$^7$OR$^7$, —CO$_2$R$^7$, —CO$_2$R$^7$, —PO(OR$^8$)$_2$, —S(O)$_n$R$^8$ (where n is 0—2), —SO$_2$NR$^9$R$^{10}$ or —CONR$^9$R$^{10}$, where $R^7$ is hydrogen, $C_1$-$C_3$-alkyl or phenyl, which may or may not be substituted by one or two amino, $C_1$-$C_4$-acylamino, $C_1$-$C_4$-alky or $C_1$-$C_4$-alkoxy groups, $R^8$ is $C_1$-$C_3$-alkyl and $R^9$ and $R^{10}$ are independently or each other hydrogen or $C_1$-$C_4$-alkyl or together form a piperidine, piperazine, morpholine or thiomorpholine ring, provided that $R^4$ and $R^5$ together form a ring of the type specified or $R^3$ and $R^5$ are each isopropyl, isobutyl or tert-butyl when X is hydrogen, nitro, or methoxy or when X is carboxyl and $R^1$ is hydroxyl, and $R^4$ and $R^5$ together form a ring of the type specified when X is CN, and that $R^4$ is not hydroxyl if m=0, and physiologically tolerated salts thereof.

2. Phenylhydrazones of formula I as claimed in claim 1, wherein $R^4$ and $R^5$ form a ring of the type specified.

3. Phenylhydrazones of formula I as claimed in claim 1, wherein $R^3$ and $R^5$ each denote branched $C_3$-$C_4$-alkyl.

4. Phenylhydrazones of formula I as claimed in claim 1, wherein X is a sulfonic acid radical or —CONR$^7$OR$^7$, —CO$_2$R$^7$, —PO(OR$^4$)$_2$, —SO$_2$R$^8$, —SO$_2$—NR$^9$R$^{10}$ or —CONR$^9$R$^{10}$.

5. Phenylhydrazones of formula I as claimed in claim 1, wherein $R^4$ and $R^5$ together form a ring of the type specified and X is a sulfonic acid radical or —CONR$^7$OR$^7$, —CO$_2$R$^7$, —PO(OR$^8$)$_2$, —SO$_2$R$^8$, —SO$_2$—NR$^9$R$^{10}$ or —CONR$^9$R$^{10}$.

6. Phenylhydrazones of formula I as claimed in claim 1, wherein $R^3$ and $R^5$ are each branched $C_3$-alkyl or $C_4$-alkyl and X is a sulfonic acid radical or —CONR$^7$OR$^7$, —CO$_2$R$^7$, —PO(OR$^8$)$_2$, —SO$_2$R$^8$, —SO$_2$—NR$^9$R$^{10}$ or —CONR$^9$R$^{10}$.

7. N-[1-(5,6,7,8-Tetrahydro-5,5,8,8-tetramethylnaphthalen-2-yl) ethylidene]-N'-[(4-methylsulfonyl)phenyl]hydazine.

8. N-[1-(5,6,7,8-Tetrahydro-5,5,8,8-tetramethylnaphthalen-2-yl) -methylidene]-N,-[(4-methylsulfonyl)phenyl]hydrazine.

* * * * *